United States Patent
Hinman et al.

(10) Patent No.: US 12,042,653 B2
(45) Date of Patent: Jul. 23, 2024

(54) ELECTRICAL APPLICATORS WITH NON-PENETRATING ELECTRODES FOR APPLYING ENERGY TO TISSUE SURFACES

(71) Applicant: Pulse Biosciences, Inc., Hayward, CA (US)

(72) Inventors: Cameron D. Hinman, Thurmond, NC (US); Wesley C. Joe, Mountain View, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 279 days.

(21) Appl. No.: 17/566,674

(22) Filed: Dec. 30, 2021

(65) Prior Publication Data

US 2023/0211161 A1    Jul. 6, 2023

(51) Int. Cl.
*A61N 1/36*    (2006.01)
*A61N 1/04*    (2006.01)

(52) U.S. Cl.
CPC ....... *A61N 1/36034* (2017.08); *A61N 1/0496* (2013.01)

(58) Field of Classification Search
None
See application file for complete search history.

(56) References Cited

U.S. PATENT DOCUMENTS

| | | | |
|---|---|---|---|
| 6,326,177 B1 | 12/2001 | Schoenbach et al. | |
| 6,463,336 B1 * | 10/2002 | Mawhinney | A61N 5/04 600/15 |
| RE40,471 E | 8/2008 | Groenke et al. | |
| 7,515,950 B2 | 4/2009 | Healy | |
| 8,000,813 B2 | 8/2011 | Schoenbach et al. | |
| 8,216,218 B2 | 7/2012 | Burns et al. | |
| 8,512,334 B2 | 8/2013 | Nuccitelli et al. | |
| 8,702,691 B2 | 4/2014 | Weber et al. | |
| 8,822,222 B2 | 9/2014 | Beebe et al. | |
| 9,101,764 B2 | 8/2015 | Nuccitelli et al. | |
| 9,700,222 B2 | 7/2017 | Quinlan et al. | |
| 9,724,155 B2 | 8/2017 | Nuccitelli et al. | |
| 9,737,701 B2 | 8/2017 | Dupelle et al. | |
| 9,962,538 B2 | 5/2018 | Axelgaard | |
| 10,850,095 B2 | 12/2020 | Ebbers et al. | |
| 11,167,125 B2 | 11/2021 | Moss et al. | |
| 2011/0015625 A1 * | 1/2011 | Adanny | A61N 1/0476 606/33 |
| 2011/0092973 A1 | 4/2011 | Nuccitelli et al. | |
| 2011/0190726 A1 | 8/2011 | Hantash et al. | |
| 2012/0136282 A1 | 5/2012 | Rosenberg et al. | |
| 2013/0046362 A1 | 2/2013 | Colthurst | |
| 2013/0165760 A1 | 6/2013 | Erlinger et al. | |
| 2014/0364797 A1 | 12/2014 | Schoenbach et al. | |

(Continued)

*Primary Examiner* — Michael W Kahelin
(74) *Attorney, Agent, or Firm* — Shay Glenn LLP (57) ABSTRACT

Applicators, systems, and methods for delivering electrical energy to a target treatment region with large area surface electrodes are disclosed. In one example, a system may include a housing, a pulse generator, and a treatment applicator coupled to the pulse generator and configured to deliver sub-microsecond high-voltage electric pulses from the pulse generator. The treatment applicator may include a first and second electrodes coupled to a substrate, where the first and second electrodes are configured to provide a uniform gap between edges of the first and second electrodes.

25 Claims, 7 Drawing Sheets

(56) References Cited

U.S. PATENT DOCUMENTS

| | | |
|---|---|---|
| 2015/0201991 A1 | 7/2015 | Zemlin |
| 2017/0245928 A1 | 8/2017 | Xiao et al. |
| 2018/0078755 A1 | 3/2018 | Kreis et al. |
| 2018/0085580 A1* | 3/2018 | Perez .................. A61N 1/0456 |
| 2022/0305275 A1* | 9/2022 | Schwarz ................ A61N 1/328 |

* cited by examiner

ELECTRICAL APPLICATORS WITH NON-PENETRATING ELECTRODES FOR APPLYING ENERGY TO TISSUE SURFACES

CROSS REFERENCE TO RELATED APPLICATIONS

None.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may be related to electrodes for the application of electrical energy to a subject, for example, a patient. More specifically, the methods and apparatuses described herein relate to the large surface area electrode applicators that may apply pulsed electrical energy (e.g., nanosecond pulsed electrical energy) to a surface of a patient's tissue, such as skin.

BACKGROUND

Electrical energy may be applied within the tissue for a variety of purposes, including for the treatment of one or more medical conditions. Electrical energy may be provided through an electrode. One of the major challenges involves finding treatment applicators with electrodes particularly suitable for treating larger surface areas. In some cases, poor or inconsistent contact between the electrode and the tissue, particularly when applying high-voltage or high power energy, may result in an uncontrolled electrical discharge, such as an arc. Furthermore, treating larger areas with high-voltage or high power energy, especially with tissue penetrating electrodes, may result in substantial pain. On the other hand, using surface electrodes may result in an unevenly distributed electric field.

These problems may be particularly acute when applying high-energy pulses, e.g., sub-microsecond electric pulses (e.g., nanosecond pulsed electrical energy), to treat patients. High-voltage, sub-microsecond pulsing may be used to treat tissue in ways that may be particularly advantageous but have been traditionally limited in the size and shape of the tissue to be treated. It would be particularly advantageous to provide methods and apparatuses that may address the above-mentioned problems.

SUMMARY OF THE DISCLOSURE

Described herein are apparatuses and methods for applying electrical energy to a subject's tissue using one or more electrodes. In particular, the methods and apparatuses (e.g., devices, and systems, including applicators) may be configured to apply high-voltage, sub-microsecond pulsing over a relatively large, flat, surface area. For example, described herein are non-penetrating electrodes that are adapted to apply a substantially uniform electric field over a large surface area (e.g., 25 mm$^2$ or greater, 30 mm$^2$ or greater, 40 mm$^2$ or greater, 50 mm$^2$ or greater, 60 mm$^2$ or greater, 70 mm$^2$ or greater, 80 mm$^2$ or greater, 90 mm$^2$ or greater, 100 mm$^2$ or greater, 120 mm$^2$ or greater, 130 mm$^2$ or greater, 140 mm$^2$ or greater, 150 mm$^2$ or greater, 160 mm$^2$ or greater, 170 mm$^2$ or greater, 180 mm$^2$ or greater, 190 mm$^2$ or greater, 200 mm$^2$ or greater, etc.) when delivering a relatively high voltage in the sub-microsecond duration. For example, the apparatuses (e.g., applicator devices or devices) described herein may be configured to apply a substantially uniform electrical field when applying electrical pulses having an amplitude of at least 0.1 kV and a duration of less than 1000 nanoseconds therebetween, without arcing. For example, an apparatus as described herein may be configured to pass electrical pulses having an amplitude of about 1 kV or greater, about 2 kV or greater, about 3 kV or greater, about 5 kV or greater, about 6 kV or greater, about 7 kV or greater, about 8 kV or greater, about 9 kV or greater, about 10 KV or greater, between about 0.1 kV and 100 kV, between about 1 kV and about 100 kV, between about 3 kV and about 100 kV, between about 5 kV and about 100 kV, etc. The pulses may be sub-microsecond pulses (e.g., less than about 1000 ns, e.g., between about 1 ns and about 1000 ns, between about 1 ns and about 950 ns, between about 1 ns and about 900 ns, between about 5 ns an about 1000 ns, between about 5 ns and about 950 ns, between about 5 ns and about 900 ns, etc.).

A substantially uniform electrical field may have approximately the same strength of the electric field over at least the region or area of the applicator surface that is between the first electrode pattern and the second electrode pattern (e.g., the gap region). The electrical field intensity may be within +/−20%, +/−15%, +/−12%, +/−11%, +/−10%, +/−9%, +/−8%, +/−7%, +/−6%, +/−5%, +/−4%, +/−3%, +/−2%, etc.

These applicators may be adapted for surface application (e.g., to skin or other tissue surfaces). In some examples the applicators may be configured or adapted for internal use, e.g., within the body. Any of these apparatuses may be used with a vacuum and may include one or a plurality of vacuum ports on the tissue-contacting side of the applicator to secure the apparatus to the tissue.

For example, these apparatuses may include a surface applicator apparatus comprising: an insulating substrate extending in a first surface; a first electrode forming a first pattern of one or more elongate traces over the first surface; a second electrode forming a second pattern of one or more elongate traces over the first surface; wherein the first pattern is adjacent to the second pattern so that there is a uniform gap separating the first pattern from the second pattern; a first conductor electrically coupled to the first electrode; and a second conductor electrically coupled to the second electrode, wherein the first conductor and the second conductor are configured to be placed in electrical communication with a pulse generator configured to deliver sub-microsecond, high-voltage electrical pulses between the first and second electrodes, respectively. The pulse generator may be operably connected to the first conductor and the second conductor.

Any of these apparatuses may include one or more a vacuum ports on the first surface and a suction channel in communication with the one or more vacuum ports, wherein the one or more vacuum ports are configured to secure the first electrode and the second electrode to a patient treatment area.

The apparatus may include an insulator within or forming the uniform gap separating the first pattern from the second pattern. In some examples, the insulator may be an insulating silicone adhesive. The tissue-contacting surface of the applicator may be substantially flat and planar, so that it may make uniform or substantially uniform contact with the tissue treatment surface.

The first electrode may comprise a first electrically conductive hydrogel or other conductive polymer matrix extending to an outer, tissue-contacting surface, and wherein the second electrode comprises a second electrically conductive hydrogel or other conductive polymer matrix extending to an outer, tissue-contacting surface. In some examples the first surface has a surface area of between 25 mm² and 100 cm² (e.g., between 50 mm² and 100 cm², between 100 mm² and 100 cm², between 150 mm² and 100 cm², between 200 mm² and 100 cm², between 250 mm² and 100 cm², between 25 mm² and 90 cm², between 25 mm² and 80 cm², between 25 mm² and 75 cm², 50 mm² or greater, 75 mm² or greater, 90 mm² or greater, 100 mm² or greater, 125 mm² or greater, 150 mm² or greater, 200 mm² or greater, 250 mm² or greater, etc.). The first pattern and the second pattern may extend over substantially the entire area of the surface (e.g., 60% or more, 65% or more, 70% or more, 75% or more, 80% or more, 85% or more, 90% or more, 95% or more, etc.).

The one or more elongate traces of the first pattern may extend in a length that is greater than 5 times a width of the one or more elongate traces (e.g., 10 times or more, 12 times or more, 15 times or more, 20 times or more, 25 times or more, etc.). Thus, the pattern of traces in the first and/or second electrodes may be substantially long and thin, forming an alternating or interdigitating/interlocking combined pattern spanning the majority of the treatment portion of the applicator.

The first electrode may include a first conductive base region on the first surface in the first pattern and a first conductive hydrogel on the first conductive base region, further wherein the second electrode may include a second conductive base region on the first surface in the second pattern and a second conductive hydrogel on the second conductive base region. The base region may refer to a conductive solid material, such as a silver, gold, carbon black, etc. that is used for the base of the electrode and to which an electrical connector may be coupled. The base region may also be referred to herein as a base connector. The hydrogel may form part of the electrode and may be layered on top of the base region. The base region may also be referred to as the "base" or base portion of the electrode, for convenience. In some cases the electrode may not include a base, but may include just a hydrogel coupled to a connector such as a wire, trace, etc.

The uniform gap separating the first pattern from the second pattern may be, for example, between 1 mm and 10 mm wide (e.g., between 0.5 mm and 15 mm, between 1 mm and 15 mm, between 1 mm and 12 mm, between 1 mm and 9 mm, between 1 mm and 8 mm, between 1 mm and 7 mm, between 1 mm and 6 mm, between 1 mm and 5 mm, between 1 mm and 4 mm, between 1 mm and 3 mm, etc.).

The surface applicator apparatus may generally be flexible. The substrate may be flexible, and the first and second (or additional) electrode may be flexible so that the entire apparatus may be substantially flexible.

In any of these apparatuses the first pattern may include a first serpentine pattern extending over the first surface and the second pattern may comprise a second serpentine pattern extending over the first surface. In some examples the serpentine patterns are sinusoidal (e.g., doubling back and forth), or spiral.

The first pattern and the second pattern may be interdigitated and separated by the uniform gap. The first pattern and the second pattern may form a plurality of parallel elongate traces over the first surface.

Any of these apparatuses, including any of the features described above, may be part of a system. The system may include a pulse generator, such as (but not limited to) a pulse generator configured to apply sub-microsecond (e.g., nanosecond) pulses having a high voltage (e.g., 0.1 kV or more, 1 kV or more, 1.5 kV or more, 2 kV or more, 3 kV or more, 4 kV or more, 5 kV or more, etc.).

For example, a system may include: an applicator comprising: an insulating substrate extending in a first surface, a first electrode forming a first pattern of one or more elongate traces over the first surface, a second electrode forming a second pattern of one or more elongate traces over the first surface, wherein the first pattern is adjacent to second pattern so that there is a uniform gap separating the first pattern from the second pattern, a first conductor electrically coupled to the first electrode, and a second conductor electrically coupled to the second electrode; and a pulse generator and configured to generate sub-microsecond high-voltage electric pulses, wherein the first conductor and the second conductor are configured to electrically couple to the pulse generator to deliver sub-microsecond, high-voltage electrical pulses between the first and second electrodes. In some examples the pulse generator further comprises a vacuum pump configured to provide suction to the applicator to secure the applicator to a treatment surface.

Also described herein are methods, including methods of using any of these apparatuses. For example, a method may include: affixing a large surface area electrode having a first surface to a patient treatment region or surface; and applying sub-microsecond pulses between a first electrode forming a first pattern of one or more elongate traces over the first surface and a second electrode forming a second pattern of one or more elongate traces over the first surface to generate a substantially uniform electric field over the large surface area electrode, wherein the first pattern is adjacent to second pattern so that there is a uniform gap separating the first pattern from the second pattern.

Any of these methods may include coupling the large surface area electrode to a pulse generator. The pulse generator may be a pulse generator as described herein (e.g., configured to apply sub-microsecond pulses, e.g., including high-voltage pulses).

Any of these methods may include affixing the applicator to the tissue to be treated by adhesively affixing the applicator to the tissue to be treated. In some examples affixing comprises flexing the first surface to conform to the patient treatment surface. In some examples affixing comprises applying suction to secure the first surface to the patient treatment surface.

Applying sub-microsecond pulses may comprise applying electrical pulses having an amplitude of at least 0.1 kV and a duration of less than 1000 nanoseconds. For example, affixing the large surface area electrode to the patient treatment region may comprise affixing the large surface area electrode to a skin surface.

Also described herein are apparatuses for delivery of electrical treatment that include a pulse generator (which may be at least partially enclosed within a housing) configured to provide sub-microsecond electric pulses, and an applicator as described herein. The applicators described herein may be referred to as treatment applicators. A treatment applicator may include a substrate, and two or more electrodes coupled to the substrate, two or more electrodes may include a first electrode and a second electrode, wherein the first and second electrodes are configured to have a uniform gap between edges of the first and second electrodes.

As mentioned, any of these apparatuses (applicators, tips, etc., which may be referred to as "applicators" for convenience) may be part of a system that includes the pulse generator coupled to the applicator and/or a source of negative pressure (e.g., vacuum).

The methods of using any of these apparatuses (devices, systems, e.g., applicators) may include affixing a large surface area applicator to a patient, before or after coupling the applicator to a configurable pulse generator. The method may also include providing sub-microsecond high-voltage pulses to the applicator, and generating electric fields directed toward a patient treatment area based on the sub-microsecond high-voltage pulses and the applicator. By virtue of the arrangement of the first and second (or more) electrodes distributed over the substrate, the applicator may apply an electric field that is substantially uniform over the applicator surface, or at least the portion of the surface between (and in some configurations including) the first and second electrodes (e.g., the gap region).

The methods and apparatuses described herein may be used to treat any appropriate tissue type, including but not limited to skin. Other tissue surfaces (including surgically exposed surface or minimally-invasively approached surfaces, may be treated. For example, any of these methods may be methods of treating a tissue (e.g., skin, organ, internal vessel, etc.) surface to which the applicator is applied. These methods may be methods of ablating (e.g., selectively killing or eliminating tissue). In particular, any of these methods may be used for cosmetic treatments, such as reducing or removing wrinkles, skin blemishes, acne, etc. The applicator may be shaped to conform to a region of a patient's body, such as all or a portion of the face (e.g., suborbital region, nose, cheeks, chin, etc.).

As mentioned above, any of these apparatuses may be configured as a device or a system, including, for example, a hand-held or hand-operated device, a computer-controlled, and/or a robotically operated, or remotely operated device. These apparatuses may be configured with one electrode pair or more than one electrode pair.

The applicators described herein may be configured as a treatment tip portion of an applicator, and/or may also include an electrical connector for connecting to a source of electrical energy. For example, the power connector may be configured to electrically connect the one or more electrodes to a power source configured to apply high-voltage power to the one or more electrodes having a peak voltage of between about 100 volts per centimeter (e.g., 0.1 kV/cm) and about 500 kV/cm (e.g., between about 0.5 kV/cm and about 500 kV/cm, between about 1 kV/cm and about 100 kV/cm, greater than about 0.1 kV/cm, greater than about 0.5 kV/cm, greater than about 1 kV/cm, etc.).

In general, the energy delivered by any of these applicators may refer to the applied electrical energy. As used herein energy is applied by the electrode(s) during the application of energy treatment or therapy. The energy treatment may be continuous or pulsed. The energy treatment may be pulsed at a single frequency or a range of frequencies, including at a modulated frequency (e.g., having a carrier frequency).

As mentioned, any appropriate electrical energy may be applied while moving the electrodes relative to the tissue. For example, applying energy may comprise applying high-voltage nanosecond electrical pulses, such as applying a train of sub-microsecond electrical pulses having a pulse width of between 0.1 nanoseconds (ns) and 1000 nanoseconds (ns). Applying high-voltage nanosecond electrical pulses may comprise applying a train of sub-microsecond electrical pulses having peak voltages of between 10 kilovolts per centimeter (kV/cm) and 500 kV/cm. Applying high-voltage nanosecond electrical pulses may comprise applying a train of sub-microsecond electrical pulses at a frequency of between 0.01 (Hz) to 10,000 Hz. Applying energy may comprise applying microsecond electrical pulses, or picosecond electrical pulses.

The methods and apparatuses described herein may be used as part of any appropriate electrical treatment or therapy. Various examples of the present disclosure are useful for applying electrical treatment to a surface of the tissue, for example, to a surface of the skin for treatment of various skin conditions, lesions, tumors, growth or abnormalities.

Any power connector may be configured to electrically connect the one or more applicators to a power source configured to apply high-voltage power to the one or more electrodes, such as (but not limited to) power having a peak voltage of between 1 kilovolt per centimeter (kV/cm) and 200 kV/cm.

Various devices and examples disclosed herein may be used for treating a relatively large treatment area by using, for example, a plurality of surface electrodes arranged as described herein. Other features and advantages of the devices and methods of the present disclosure will become apparent from the following detailed description of one or more implementations when read in view of the accompanying figures.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control performance of any of the steps, including but not limited to: displaying, communicating with the user, analyzing, modifying parameters (including timing, frequency, intensity, etc.), determining, alerting, or the like.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 3A-3G illustrate an example of a large surface area applicator.

DETAILED DESCRIPTION

Described herein are apparatuses (e.g., devices, systems, etc. including applicators) adapted to be used for the application of electrical energy into a target tissue. In particular, the applicators described herein comprise large area, non-penetrating electrodes especially useful for treating a large surface area, including, but not limited to, treating various skin conditions, various benign lesions, acne, and tattoo removal. The apparatuses and methods described herein may also be used for internal (e.g., non-dermal) applications, applying energy to an internal surface of a tissue, organ or vessel. These apparatuses and methods may be particularly well adapted to apply high-voltage, sub-microsecond pulsed energy to a tissue without arcing.

Figure 1:
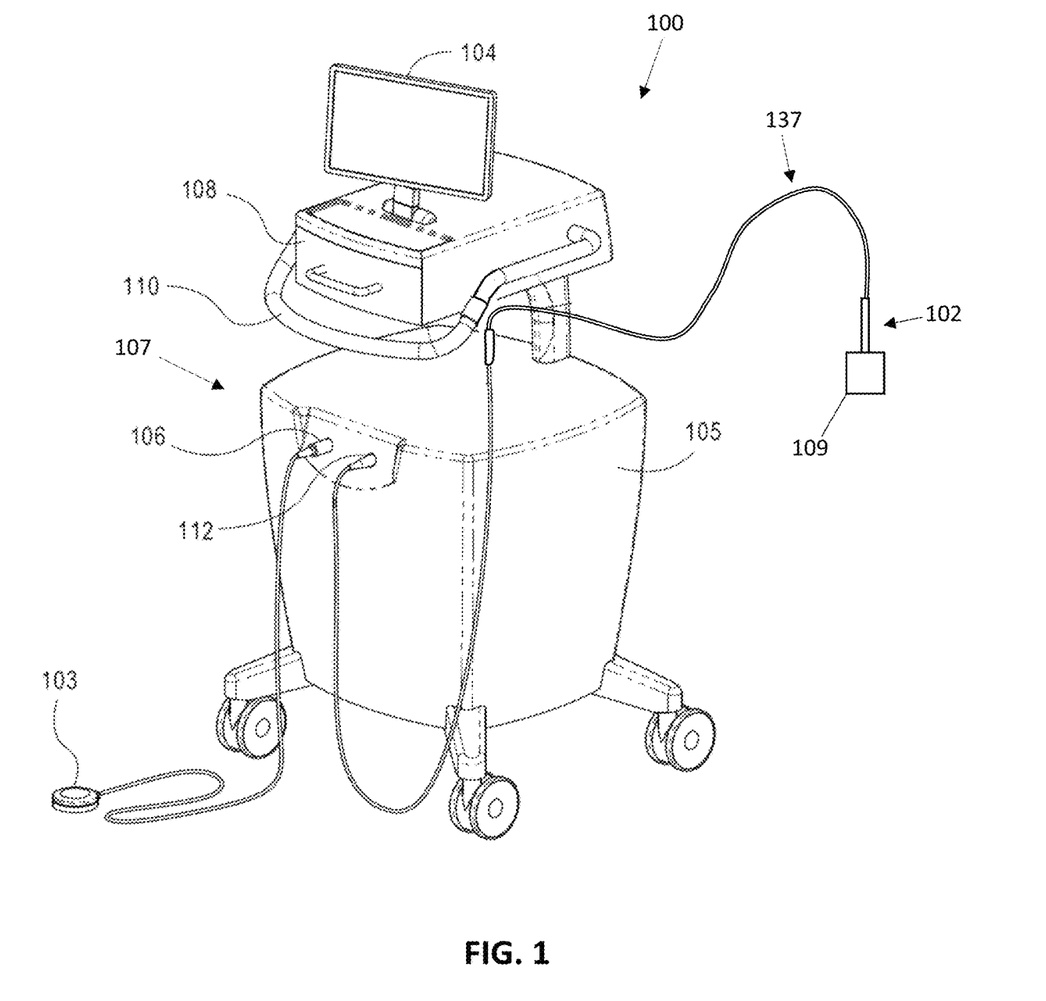
FIG. 1 illustrates one example of a system, including an applicator as described herein and a pulse generator to which the applicator may be coupled, for delivery of high voltage, fast pulsed electrical energy.

Any of these apparatuses may include a pulse generator as part of a system including the applicator (e.g., unitary applicator or an applicator comprising a treatment tip releasably coupled to a handle, etc.). For example, FIG. 1 illustrates one example of a system 100 that may be used with or may incorporate, any of the applicators described herein. The system shown in FIG. 1 (also referred to herein as a high-voltage system or a sub-microsecond pulse generation system) for delivering high-voltage, fast pulses of electrical energy that may include an applicator 102, a pulse generator 107, footswitch 103, and user interface 104. Footswitch 103 is connected to housing 105 (which may enclose the electronic components) through a cable and connector 106. The applicator tool 102 may include electrodes (e.g., large surface area, non-penetrating electrodes) and may be connected to housing 105 and the electronic components therein through a cable 137 and high-voltage connector 112. Applicators may be designed as hand-held devices, as devices that can be coupled to a robotic (movable) arm, or in any other appropriate configuration. Examples of applicators are described in greater detail below. The system 100 may also include a handle 110 and storage drawer 108. The system 100 may also include a holder (e.g., holster, carrier, etc.) (not shown) which may be configured to hold the elongate applicator tool 102.

The pulse generator 107 may be configured to safely and reliably to deliver microsecond, nanosecond, picosecond, etc. voltage pulses, and may include or induce an electric field with a pulse width of between 0.1 nanoseconds (ns) and less than 1000 nanoseconds, or shorter, such as 1 picosecond, which may be referred to as sub-microsecond pulsed electric field. The associated electric fields may have high voltage densities, such as between about 1 to 5 kilovolts per centimeter (kV/cm), 10 kV/cm, 20 kV/cm, 100 kV/cm, 200 kv/cm or higher. Treatment of biological cells may use a multitude of periodic pulses at a frequency ranging from 0.1 per second (Hz) to 10,000 Hz. The electric fields may be delivered to human and/or non-human patients, including animals. A user may operate the apparatuses described herein on any feasible subject. The user may be a physician (doctor, surgeon, etc.), medical technician, nurse, or clinician.

Thus, the application of high-voltage, fast (e.g., microsecond or sub-microsecond) electrical pulses may include applying a train (e.g., series or sequence) of electrical pulses having a pulse width, for example, of between 0.1 nanoseconds (ns) and 1000 ns. Applying high-voltage, fast electrical pulses may include applying a train of sub-microsecond electrical pulses having peak electric fields of between, for example, 1 kilovolt per centimeter (kV/cm) and 200 kV/cm. Applying or generating high-voltage, fast electrical pulses may include applying or generating a train of sub-microsecond electrical pulses at a frequency, for example, of between 0.1 per second Hz to 10,000 Hz.

In some cases, the applicator 102 may include a treatment tip portion 109. The treatment tip portion may be single-use or limited use and may be removably attached to a handle or other region. For example, the treatment tip portion may be configured as a disposable applicator tip 109 (also referred to as a treatment tip) that may releasably couple to a handpiece or handle of the elongate applicator 102. In some examples, the applicator tip 109 may be adapted to make an electrical, mechanical, and/or pressure connection, as will be described in greater detail below. In some examples the system 100 may include, or may be configured to operate with, a source of negative pressure (e.g., suction, vacuum, etc.). In some examples, the handle of the applicator tool 102 may include a self-contained source for generating suction that may be used to apply suction at the applicator tip 109.

A human operator may select a number of electrical pulses, an amplitude, a pulse duration, and/or frequency information, for example by inputting such parameters into a numeric keypad or a touch screen of user interface 104, and/or by selecting one or more pre-set programs. In some examples, the pulse width can be varied. A microcontroller may send signals to pulse control elements within the system 100. In some examples, fiber optic cables are used which allow control signaling while also electrically isolating the contents of the metal cabinet with sub-microsecond pulse generation system 100, e.g., the high-voltage circuit, from the outside. In order to provide further electrically isolation, system 100 may be battery powered instead of being powered from a wall outlet.

The elongate applicator tool 102 may be hand-held (e.g., by a user) or it can be affixed to a movable arm of a robotic system, and its operation may be at least partially automated or fully automated, including computer controlled.

As mentioned, the methods and apparatuses described herein include applicators that include one or more sets (e.g., an array) of non-penetrating electrodes (in some cases within the applicator tip 109) for applying electrical energy to a tissue. In some examples, the electrodes may be electrically coupled by the cable 137 to the pulse generator 107. In this manner, short duration, high-voltage pulses may be delivered to the electrodes, and the electrodes may generate corresponding therapeutic electric fields. The applicator (e.g., the elongate applicator tool 102) may include the applicator tip 109 and a handle portion. The applicator tip 109 and handle may be separate, or may be combined into a single, unitary applicator. In some examples the applicator tip 109 may be removable from the handle so that multiple different tips, including different types of tips, can be coupled to the handle. The handle and/or the tip may include a source of negative pressure (e.g., suction or vacuum) that may be applied through the electrode in order to modify the contact between the tip, and in particular the electrode(s) of the tip, and the tissue. In particular, the handle may include a self-contained source of vacuum.

Also described herein are applicators that are adapted be placed on the tissue that may be flexible, e.g., may be formed of a flexible substrate, that may conform to the tissue surface. Any of these apparatuses may include a tissue-contacting surface that may include a hydrogel and/or adhesive material. In some examples these apparatuses are configured to couple to the tissue surface and may be held in place by the hydrogel and/or adhesive; in some examples suction may also or additional be used. In some examples the applicator does not include a handle region but may be placed on or against the tissue and left in place for a treatment, or for repeated treatments.

Large Surface Area Electrodes

Described herein are applicators (e.g., applicator devices, applicator tips, etc.) that include electrodes which may be configured to cover a large surface area. For example, such applicators may be especially useful for treatment of acne or similar conditions that needs a large area coverage. These electrodes also may be non-penetrating electrodes (e.g., surface electrodes) that allow reducing treatment pain, which is especially beneficial when treatment a larger area. For example, the electrodes may be configured as an elongate strip (or two or more interleaved strips) that are surrounded and/or separated by an insulating material (insulator). The electrode may be a surface electrode that includes a conductive hydrogel.

For example, some large surface area electrodes may include a plurality of electrode strips that are arranged in a two-dimensional (2D) pattern. The electrodes strips may be arranged in parallel and may be separated from each other by an insulator. In some examples, the electrode strips may be separated by a constant and uniform spacing distance or "gap". For example, in some examples, edges of the electrode strips may be separated from each other by a gap of between 0.1 mm and 15 mm (e.g., between 0.1 mm and 13 mm, between 0.1 mm and 12 mm, between 0.1 mm and 11 mm, between 0.1 mm and 10 mm, between 0.1 mm and 9 mm, between 0.1 mm and 8 mm, between 0.1 mm and 7 mm, between 0.1 mm and 6 mm, between 0.1 mm and 5 mm, between 0.5 mm and 15 mm, between 0.5 mm and 12 mm, between 0.5 mm and 10 mm, 1 mm or more, 2 mm or more, 3 mm or more, etc.) or any feasible distance. The edge or corners of the two-dimensional strips or shapes may be rounded or curved. In some examples, the electrode strips may be separated from each other by any appropriate insulating material, such as an adhesive (e.g., silicone) and/or air. The electrode strips may be formed from a conductive hydrogel (similar to an RF ground pad or an AED defibrillator pad electrode material). In any of these examples the electrode strips may be arranged as alternating strips of different polarity (e.g., high-voltage out/return). The 2D pattern of electrode strips may be arranged on a non-conductive substrate (which may be referred to as a carrier substrate) such as a flex-circuit material, e.g., Kapton™ or other polymeric material. In some examples the substrate is configured to include channels, passages, or openings for forming a suction port. The substrate may be configured to have a thickness that allows it to be flexible.

Any of these large surface area electrodes may therefore include conductive hydrogels as part of the electrode(s). The hydrogel may generally have a high moisture content, which may reduce skin impedance between the electrodes and the skin. Although the high surface-area electrode applicators described herein are particularly well suited for use on skin, they may be used, and adapted for use, with any appropriate tissue (including organ tissue, e.g., heart, lung, etc.) or surgically treated tissue (cut tissue), and/or may be applied as a 2D surface on a surgical device, such as a catheter, tube, etc., that may be inserted into a tissue.

In general, the hydrogel may be used in combination with a highly conductive substrate (e.g., silver ink) to maintain or provide an equal voltage potential across an electrode strip. Thus, for example, the hydrogel may be applied over and in electrical contact with a metal or carbon electrode.

These large surface-area applicators (e.g., hydrogel-containing electrodes) may be non-penetrating electrodes and may be configured to minimize tissue trauma. For example, the hydrogel may act as an adhesive that helps maintain tissue contact to eliminate or reduce arcing through air gap formation between the tissue and the electrode. The electrode strips (e.g., conductors) size may be relatively large. The current output and/or voltage from the pulse generator 107 may be adjusted to enable long electrode strips and therefore larger surface area applicator electrodes to provide pulsed electric fields as described above. The large surface area electrode applicators described herein may be used with any of the pulse generators and/or power supplies described herein (see, e.g., FIG. 1). The large surface area electrode applicators also may be used in any of the treatments described, including but not limited to skin condition treatments, such as general benign lesions, acne, tattoo removal, etc.

Figure 2:
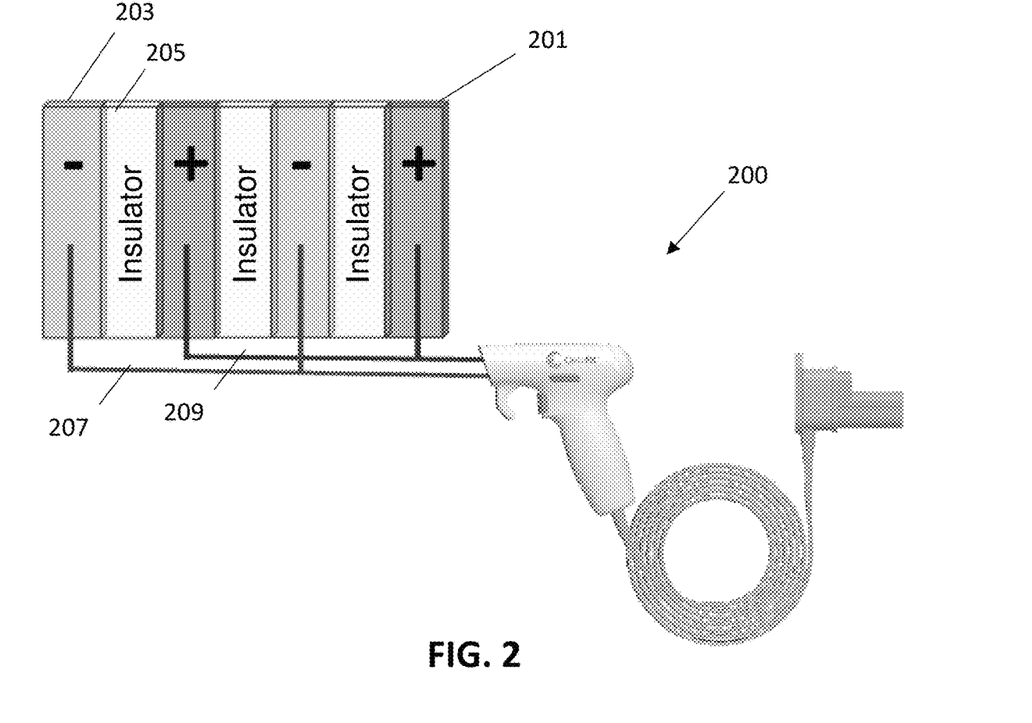
FIG. 2 illustrates one example of an applicator including an applicator with a large surface area.

As mentioned, the large surface area electrode applicators described herein may include a conductive hydrogel or other conductive polymer matrix separated by insulation. The insulation region could be an area of higher resistivity to help distribute the energy more uniformly. FIG. 2 schematically illustrates an example of an applicator 200 including an electrode pattern 201 with a large surface area. The electrode pattern 201 may be an example of a large surface area (in some cases, non-penetrating) applicator and include a plurality of alternating electrode (in some cases, including hydrogel) strips 203 which may be separated by an insulator 205. The insulator 205 may form a uniform gap between edges of the electrode strips 203. In some examples, the insulator 205 may be air, thus, the gap between the edges of the electrode strips 203 may be due to (formed by) placement of the electrode strips 203. The electrode strips 203 are shown in parallel, but other configurations are contemplated, as described below in conjunction with FIGS. 7-9. In this example, the applicator 200 may include insulated conductors 207 and 209 that couple the electrode strips 203 to a controllable voltage source, such as the pulse generator 107 of FIG. 1 (not shown). In some examples, alternating electrode strips 203 may be associated with different polarities. In this example, parallel strips of conductive hydrogel (similar to RF ground pads or AED defibrillator pads), may be separated by a gap by an insulated adhesive (such as silicone). Different examples of the electrode pattern 201 may include alternating electrode strips 203 separated by a gap. Generally, the gap separation in the same apparatus may be constant, but different apparatuses (e.g., different electrode patterns) may have different gap separations. The electrode strips 203 may be formed into the 2D pattern on a non-conductive carrier substrate. The hydrogel is applied onto a highly conductive substrate (e.g., silver ink) to maintain or provide an equal voltage potential over the electrode strips 203.

In some examples, the applicator 200 may be configured to receive a vacuum. The vacuum may be used to attach or affix the electrode strips 203 onto a treatment area of a patient. Using a vacuum to attach or affix electrodes to the patient may be particularly advantageous when the electrodes are non-penetrating electrodes having a large surface area. In some other examples, the applicator 200 may include a vacuum pump contained within a handle to provide the vacuum. Alternatively, a vacuum pump may be remotely located and coupled to applicator 200 by any feasible hose or tubing.

By carefully controlling the gap between adjacent electrode strips 203, the area of the electrode pattern 201 may be made to treat an arbitrarily large surface. In some cases, the electric field density (e.g., volts-per-centimeter or V/cm) that may be delivered to a patient may be based at least in part on the gap between the electrode strips 203. Thus, a well-controlled (e.g., constant or uniform) gap between two or more electrode strips may be made to provide treatment to a large area. In some examples, the gap may be a serpentine formed by interdigitated electrode strips 203. The serpentine gap may be made to cover a large surface area. That is, an increased electrode (applicator) area may be obtained by increasing the area covered by the well-controlled gap.

Figure 3A:
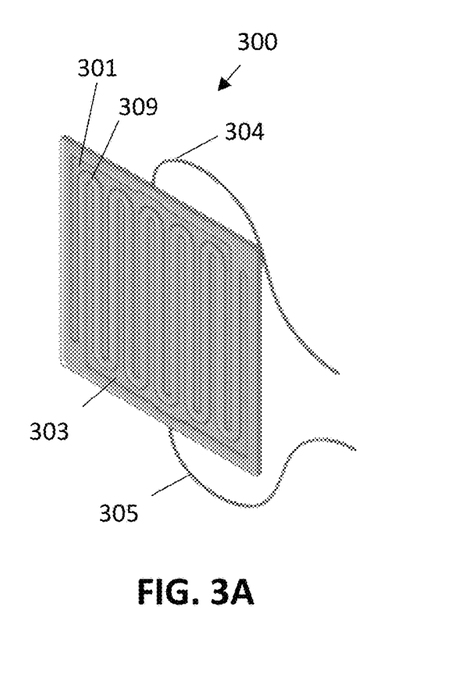
FIG. 3A shows a perspective view of a 2D applicator configured to cover a large surface area.
Figure 3B:
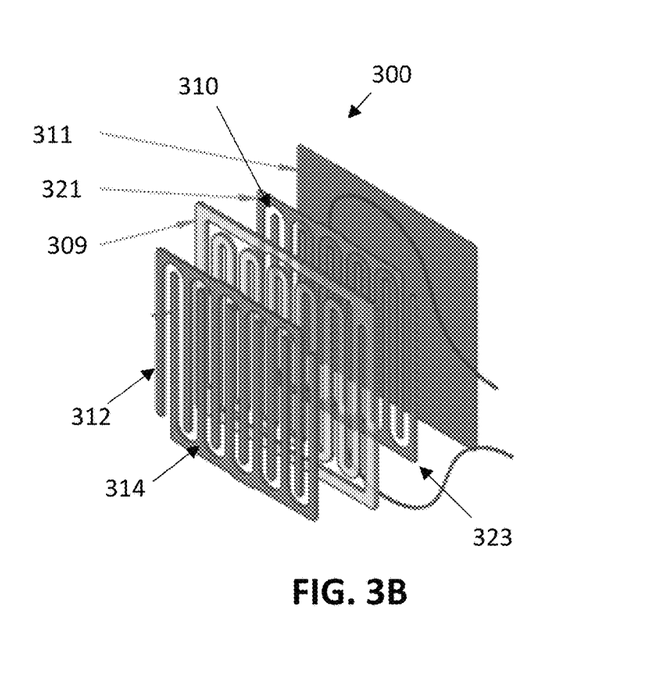
FIG. 3B shows an exploded view of the applicator, illustrating a substrate, the first electrode, the second electrode, and the insulator.

FIGS. 3A-3G illustrate an example of a large surface area, non-penetrating applicator in greater detail. In particular, FIG. 3A shows a perspective view of a 2D pair of electrodes 300 configured to cover a large surface area. The plurality of electrodes 300 forming the applicator may include a first electrode 301 and a second electrode 303. In this example, the first and second electrodes 301 and 303 may each include a pattern of elongate traces that are arranged along the treatment tip portion of the applicator so that the elongate traces forming the first electrode pattern are uniformly spaced by a gap from the elongate traces forming the second electrode pattern. Any number of electrode patterns (electrodes) may be used, but the electrodes are typically paired with each electrode pattern of the pair separated from each other by a uniform gap distance. In some examples, as shown in FIGS. 3A-3G, the patterns of elongate traces forming the electrodes may include multiple interleaved (in some cased interdigitated or interlocked) U-shaped electrode strips (e.g., electrodes) arranged in a 2D (surface) pattern. In this example, each electrode includes a base region formed of a solid conductor (e.g., gold, silver, carbon black, etc.) onto which a conductive hydrogel is coupled. The first 301 and second 303 electrodes in this example include a first conductive base 321 and a second conductive base 323 (shown as a single layer with two interdigitating members in FIG. 3B) that are connected to conductors 304 and 305, respectively, and separated by an insulator 309 (e.g., an electrically insulating silicone adhesive). A first conductive hydrogel 312 may be applied on top of the first conductive base 321 and a second conductive hydrogel 314 may be applied on top of the second conducive base 323. In FIG. 3B the first and second conductive hydrogels are shown as part of the same layer but are separated by a gap distance. In some examples apparatus 300 may be attached or integrated into any appropriate applicator or applicator tip. In some examples, the applicator 300 may be configured to include one or more vacuum ports that receive a vacuum and use the received vacuum to attach and hold the tissue-contacting surface of the surface applicator 300 onto a treatment area of a patient. The use of the vacuum can enable arbitrarily large surface area applicators to be used. In some cases, the use of the vacuum can provide a uniform and consistent contract between the applicator surface and the patient that may reduce arcing and increase patient comfort.

FIG. 3B shows an exploded view of the applicator 300, illustrating a substrate 311, the first conductive base 321 and the first hydrogel 312, forming the first electrode 301, the second conductive base 323 and the second conductive hydrogel 314, forming the second electrode 303, and the insulator 309. Notably, the insulator may form the gap between the first and second electrodes. As shown, the gap 310 may be uniform having a relatively constant width and may be continuous. The gap 310 may be any feasible amount including, but not limited to 1 mm, 2 mm, 3 mm, 4 mm, 5 mm, and so forth. In some examples, different applicators may have different gaps. For example, a first electrode pattern may have a gap of 1 mm, a second electrode pattern may have a gap of 2 mm, and so on. The gap 310 may be serpentine. In some cases, the gap 310 may be formed by the space between the interdigitated first and second electrodes 301 and 303. In some other examples, the applicator may include one or more additional electrodes.

Figure 3C:
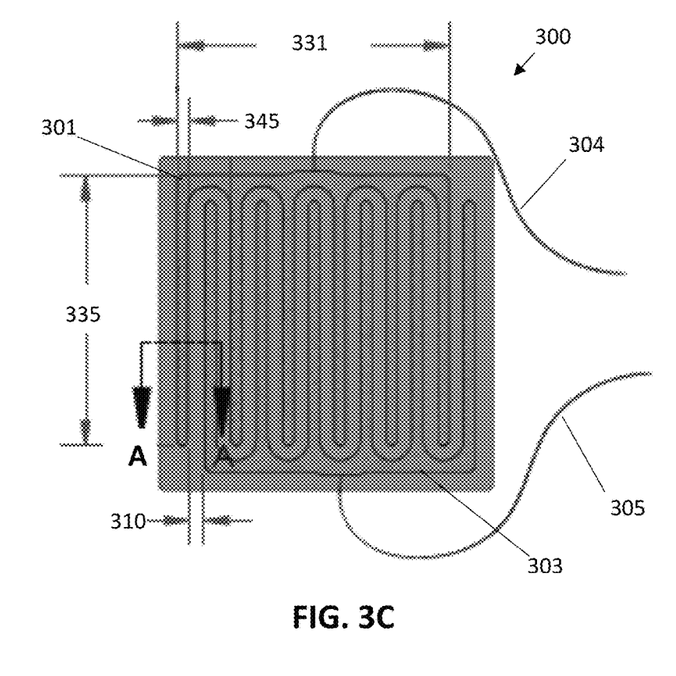
FIG. 3C shows a front view of the applicator shown in FIG. 3A.
Figure 3D:
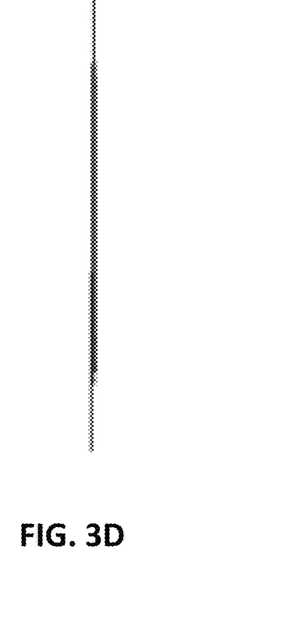
FIG. 3D shows a side view of the applicator of FIG. 3A, illustrating that the structure may be relatively flat and thin.
Figure 3E:
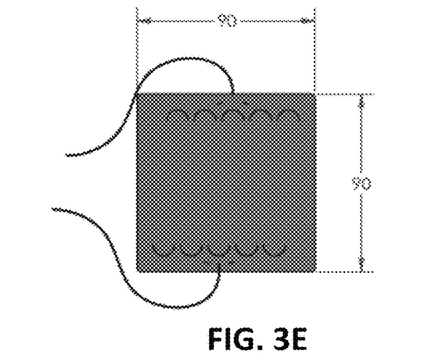
FIG. 3E shows an example of the back of the applicator shown in FIGS. 3A-3D.
Figure 3F:
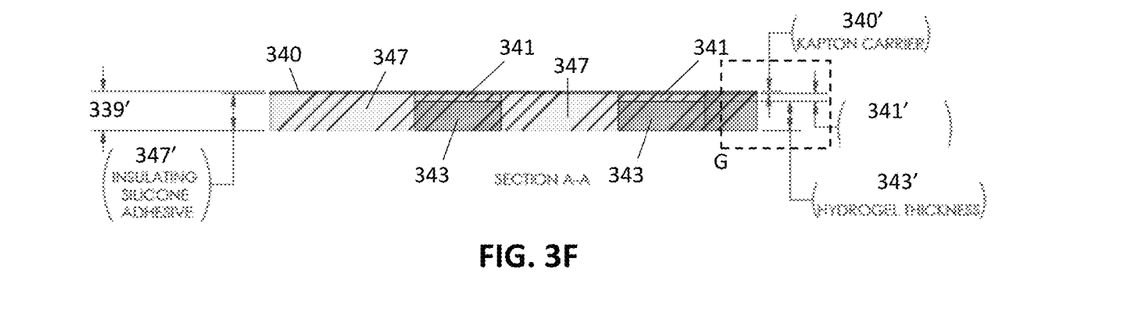
FIG. 3F shows a section through the applicator of FIGS. 3A-3E.

FIG. 3C shows a front view of the applicator 300 of FIG. 3A. As shown, the applicator 300 may include the first electrode 301, the second electrode 303, and conductors 304 and 305. The conductors 304 and 305 may couple the first electrode 301 and the second electrode 303, respectively to a pulse generator (not shown). Any appropriate dimensions may be used. For example, larger or smaller electrodes and/or insulator regions may be used. In the example shown in FIG. 3C, the relatively constant gap 310 between adjacent patterns of electrodes may be, e.g., between 1 mm and 8 mm (e.g., between 2-6 mm, between 3-5 mm, about 4 mm, etc.), however in other examples the gap 310 may be larger or smaller. FIG. 3D shows a side view of the applicator 300 of FIG. 3A, illustrating that the structure may be relatively flat and thin. FIG. 3E shows an example of the back of the applicator 300 shown in FIGS. 3A-3D. A section through region A-A in FIG. 3C is shown in FIG. 3F. In some examples the interdigitating first electrode pattern 301 and second electrode pattern 303 may have a width 331 that is, e.g., between about 15 mm and about 100 mm and a height 335 of between about 15 mm and about 100 mm. Although the example shown has a square configuration other configurations may be used, including, e.g., rectangular, circular, hexagonal, etc.

Figure 3G:
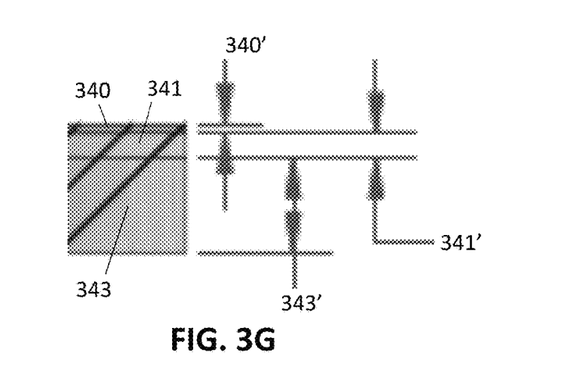
FIG. 3G shows an enlarged view of region G in FIG. 3F.

As shown in FIGS. 3D, 3F and 3G, the applicators described herein may be substantially flat and thin, which may also allow them to be flexible for application against the tissue. For example, the applicator may have a thickness 339' of between about 0.5 mm and about 7 mm (e.g., between about 0.5 mm and about 5 mm, between about 0.5 mm and about 3 mm, etc.). In some examples the applicator may include a thin substrate 340 (e.g., having a substrate thickness 340' of between about 0.05 and 0.4 mm, between about 0.05 mm and 0.15 mm, etc.), onto which the first electrode pattern and the second electrode pattern are layered. The substrate may be an insulative material, such as Kapton. The electrodes may be formed of a conductive base (e.g., solid conductor) and a conductive hydrogel. For example, the first and second electrode patterns may be formed of a conductive electrode base portion 341 (e.g., having a base thickness 341' of between 0.1 mm and 0.4 mm, e.g., between about 0.15 mm and about 0.4 mm, between about 0.2 and about 0.3 mm, etc.) underlying a conductive hydrogel 343 (e.g., having a hydrogel thickness 343' of between about 0.5 mm and 5 mm, e.g., between 0.5 mm and about 3 mm, between about 0.5 mm and about 2 mm, between about 0.75 mm and about 1.5 mm, etc.). The elongate traces may have a trace width 345 of, e.g., between about 0.5 mm and about 10 mm (e.g., between about 0.5 and about 7 mm, between about 1 mm and about 5 mm, etc.). The region surrounding and between the electrodes may be insulated and may be an adhesive. For example, in FIG. 3F, an insulating silicone adhesive 347 surrounds the electrodes so that the skin-contacting surface is flat. In FIGS. 3C, 3F and 3G, the thicknesses are show as the space between pairs of arrows.

Figure 4:
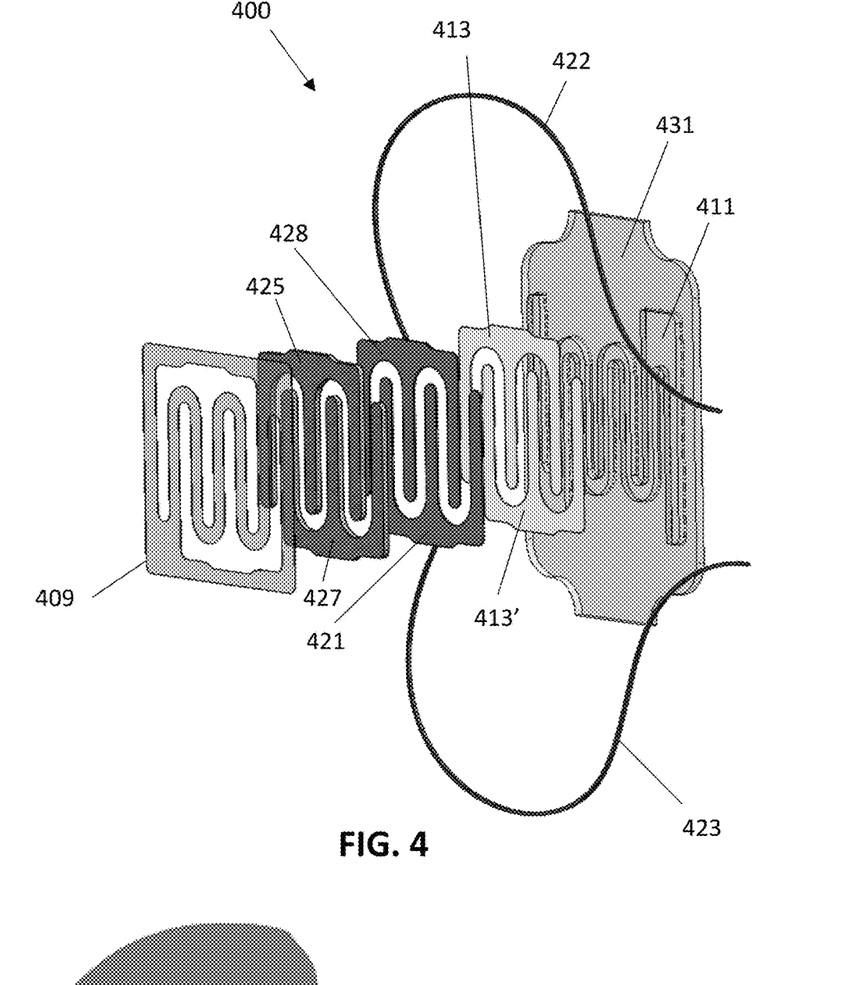
FIG. 4 shows an exploded view of another example of an applicator as described herein.

FIG. 4 shows an exploded view of another example of an applicator 400 as described herein. In FIG. 4, the applicator 400 includes a substrate 411 onto which the first and second electrodes are formed and separated by an insulative material 431 (e.g., an insulating adhesive). The insulative material 431 is also layered on the substrate, adjacent to the electrodes. The first electrode is formed of a first electrically conductive base 428 and a first conductive hydrogel 425. The second electrode is formed of a second electrically conductive base 421 and a second conductive hydrogel 427. An insulator 409 surrounds the first and second electrodes; the insulating material may be an insulating elastomeric material (and/or an adhesive material). The first electrode and the second electrode may be an example of a large surface area applicator; additional electrodes may be included.

The first electrode (e.g., the first electrically conductive base 428) may be coupled to a first conductor 422 and the second electrode (e.g., the second electrically conductive base 421) may be coupled to a second conductor 423. Similar to the conductors 207 and 209 of FIG. 2, the first and second conductors 422 and 423 may couple the first electrode pair to a pulse generator (not shown) to receive sub-microsecond, high-voltage pulses and generate corresponding electric fields.

The electrodes and insulators may be formed by a molding and/or 3D printing process. The gap region between the first electrode and the second electrode may be constant and may be filled by the insulator. In some examples, the width of the gap region may be selected to affect the strength of the electric field provided to the patient.

In some examples, the applicator 400 may receive a vacuum through a hose, tube, or the like (not shown). The vacuum may enable applicator electrodes (e.g., any electrodes associated with the applicator 400) to affix themselves to a treatment area of the patient. The vacuum may be particularly advantageous in securing, flattening and attaching applicator electrodes having a large surface area to the treatment area.

The applicator 400 also includes an adhesive 413 that may be disposed between the substrate 411 and the first electrically conductive base 428 of the first electrode; the same or a different adhesive 413' may be disposed between the substrate 411 and the second electrically conductive base 421 of the second electrode. The adhesive 413 may be e.g., 3M 300LSE, and may adhere the first electrode and/or the second electrode pair 405 to the substrate 411.

Figure 5:
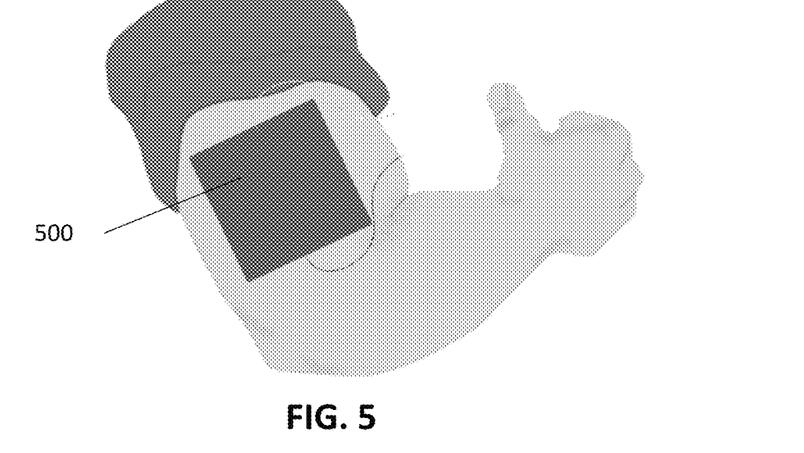
FIG. 5 illustrates an example of an applicator 500 applied to a region of a subject's skin.

FIG. 5 illustrates an example of an applicator 500 applied to a region of a subject's skin. The applicator 500 may be one example of a large surface area, non-penetrating applicator. In some examples, the applicator 500 may be coupled to a pulse generator (not shown) that can provide sub-microsecond, high-voltage energy.

In any of the electrodes and/or applicators described herein (including large surface area electrodes), the configuration of the electrodes and insulators may be arranged so that an associated electric field (E-field) density is evenly distributed. Generally, when electrodes include one or more tight-radiused turns, the resulting E-field may be unevenly distributed in the region of the tight-radiused turn. One illustrative example may include electrodes with an interlocking U design, such as the electrodes illustrated in FIGS. 3A-3F or FIG. 4. The tight-radiused corners may generate a relatively higher E-field, particularly compared to regions of the electrodes that are not associated with tight-radiused corners. Thus, in some examples, it may be beneficial to provide electrodes having relatively longer regions of straight electrode edges which may provide a uniform E-field.

Figure 6A:
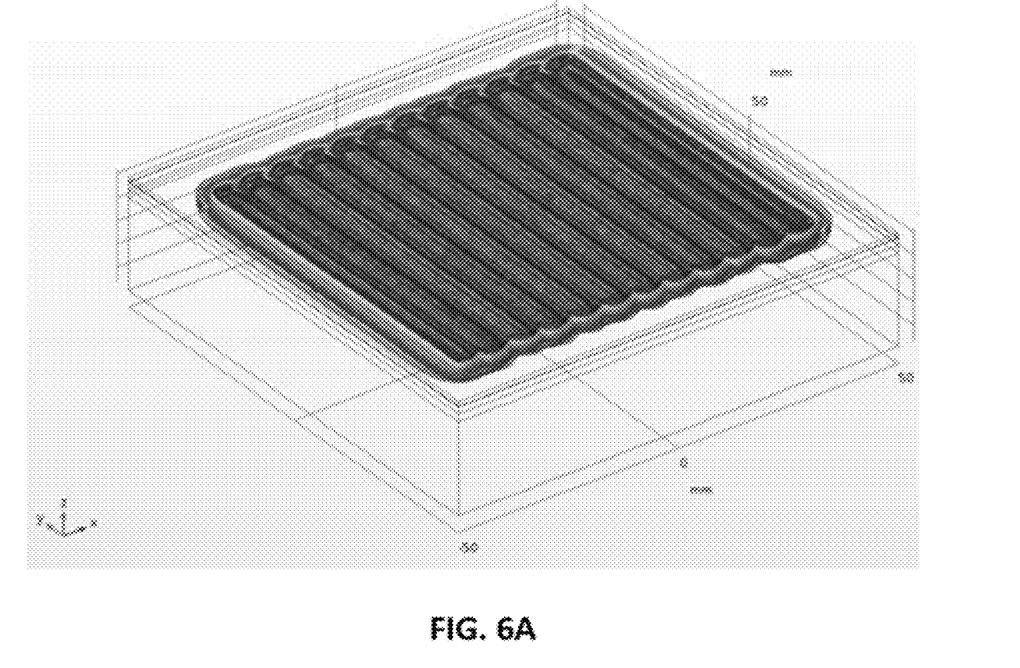
FIG. 6A-6B illustrate simulated electrical field ("E-field") distributions for an example applicator as described herein.
Figure 6B:
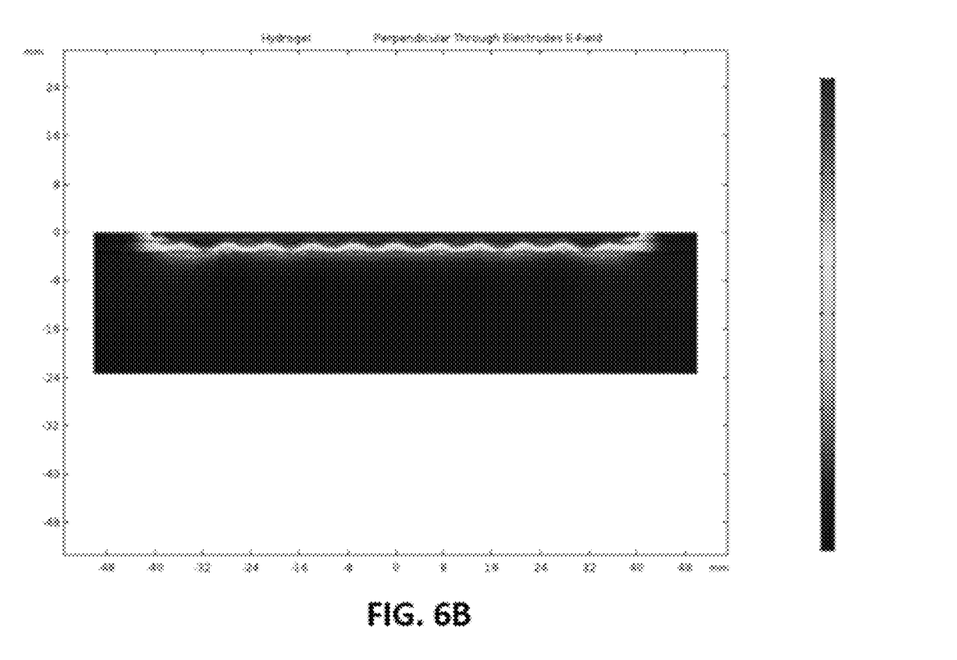

For example, FIGS. 6A-6B illustrate simulated E-field distributions for an example applicator as described herein. In some examples, the E-field distribution may be associated with large surface area electrodes. In FIGS. 6A and 6B, a heat mapping shows the current density/field concentration of one example of a large surface-area applicator electrode having a particular electrode width and spacing between electrodes. For example, a 90×90 mm applicator may include electrode strips that are approximately 4 mm wide and have a 3 mm spacing (e.g., gap) to distribute field as evenly as possible. The heat maps show an electric field density mapping that is fairly uniform across the surface, as shown in both FIGS. 6A and 6B. The large surface area electrodes may be coupled directly to a surface (e.g., skin) using conductive hydrogel. In this example, area between the electrodes may be insulated using a silicone adhesive, preventing or reducing arcing between electrodes.

Figure 7:
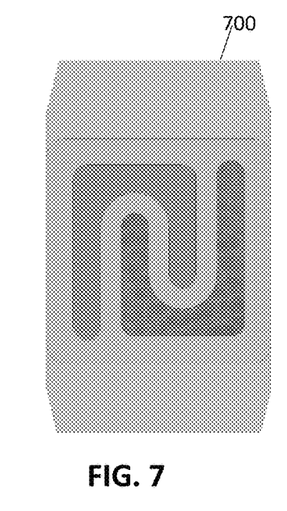
FIG. 7 shows the electrodes of an applicator arranged as interlocking U-shapes and configured as a 20×20 mm array.
Figure 8:
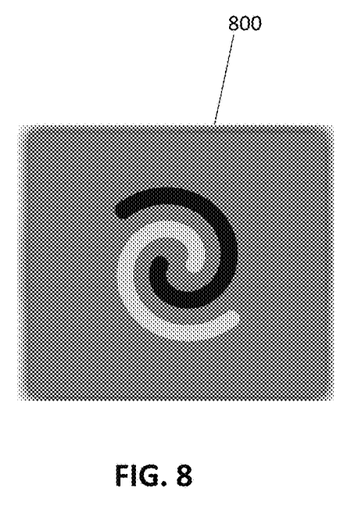
FIG. 8 shows electrodes of an applicator arranged as interlocking helixes.
Figure 9:
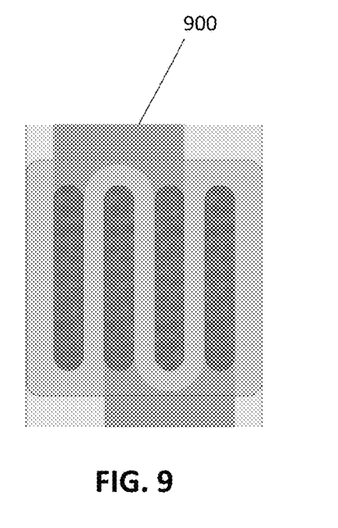
FIG. 9 shows electrodes of an applicator 900 arranged as full-length rows.

FIGS. 7-9 illustrate examples of alternative arrangements of electrodes (and/or hydrogel that may be coupled to the electrodes) that may be used with any of the applicators described herein. FIG. 7 shows (similar to that shown in FIG. 3A-3C), the electrodes of an applicator 700 arranged as interlocking U-shapes and configured as a 20×20 mm array. FIG. 8 shows electrodes of an applicator 800 arranged as interlocking helixes. FIG. 9 shows electrodes of an applicator 900 arranged as full-length rows.

Figure 10:
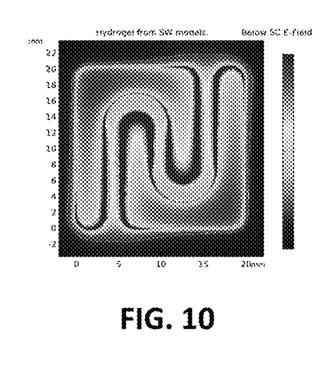
FIG. 10 shows the E-field density for electrodes similar to those depicted in FIG. 7.
Figure 11:
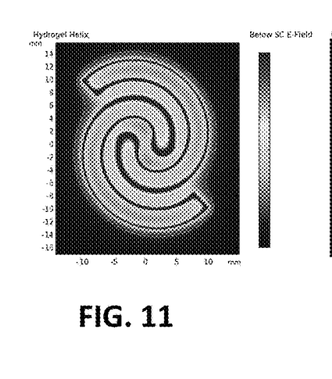
FIG. 11 shows a modeled E-field density distribution for helix electrodes such as the electrodes depicted in FIG. 8.
Figure 12:
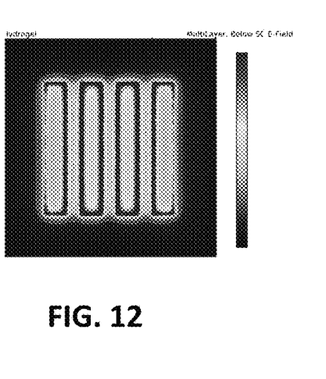
FIG. 12 shows a modeled E-field density distribution of the applicator 900 of FIG. 9.

Any of these electrode configurations may be modified or adjusted to provide a more uniform arrangement of electric field density. FIGS. 10-12 illustrate electric field modeling of the large surface area applicators shown in FIGS. 7-9, respectively. FIG. 10 shows the E-field density for electrodes similar to those depicted in FIG. 7. Regions having sharp bends (e.g., tight-radiused corners) are predicted to have a larger E-field strength than straight or lower curvature regions. FIG. 11 shows an E-field density for helix electrodes such as the electrodes depicted in FIG. 8. This interlocking helical pattern may provide a relatively even E-field, excepting toward the center of the helical pattern. As shown, the center may have a low spot (e.g., low strength) E-field. The low spot may be addressed with a small shape modification of the applicator 800. Thus, the applicator 800 may provide a way to get an even E-field in a different shape compared to interlocking U-shape of FIG. 7. FIG. 12 shows the modeled E-field distribution of the applicator 900 of FIG. 9. In general, the use of parallel conductor fingers may act as individual rows of electrodes, allowing a more uniform E-field. Electrode width and spacing (gap) of the applicator 900 may be optimized to provide a consistent field depth to the thickness of the tissue, such as epidermis and dermis (e.g., approximately 2 mm, 3 mm, 4 mm, 5 mm, etc.). The hydrogel, which may coat or be a part of any of the electrodes described herein) may also act to disperse current so that there are no current concentration points, which may reduce tissue trauma. A more uniform current distribution may also reduce localized heating effects from joule heating.

In any of the electrodes (applicators) shown herein, the conductive hydrogel may be adapted to reduce skin impedance and/or improve conductivity, for example by adjusting or adding the salt within the hydrogel.

Any of these applicators may include a release layer that may be removed so that the electrodes may be applied to the skin. The applicators may be packaged in a sealed package, to maintain a high moisture content and protect the sensitivity of the hydrogel to humidity. Thus, any of these hydrogel electrodes may be sealed in moisture barrier packaging, such as a foil layer (poly-foil or paper-poly-foil) packaging.

Although the examples of large surface area applicator electrodes shown in FIGS. 7-9 are 20 mm×20 mm, larger (or smaller) sizes may be used. For example, the large surface-area applicator electrodes may be between 5 mm and 200 mm in diameter or larger (e.g., 10×20 mm, 30×30 mm, 40×40 mm, 30×50 mm, 50×50 mm, 60×60 mm, 70×70 mm, 80×80 mm, 90×90 mm, 100×100 mm, etc.). Rectangular, circular, square, ovoid or other shape large surface area electrode applicators may be used.

Figure 13:
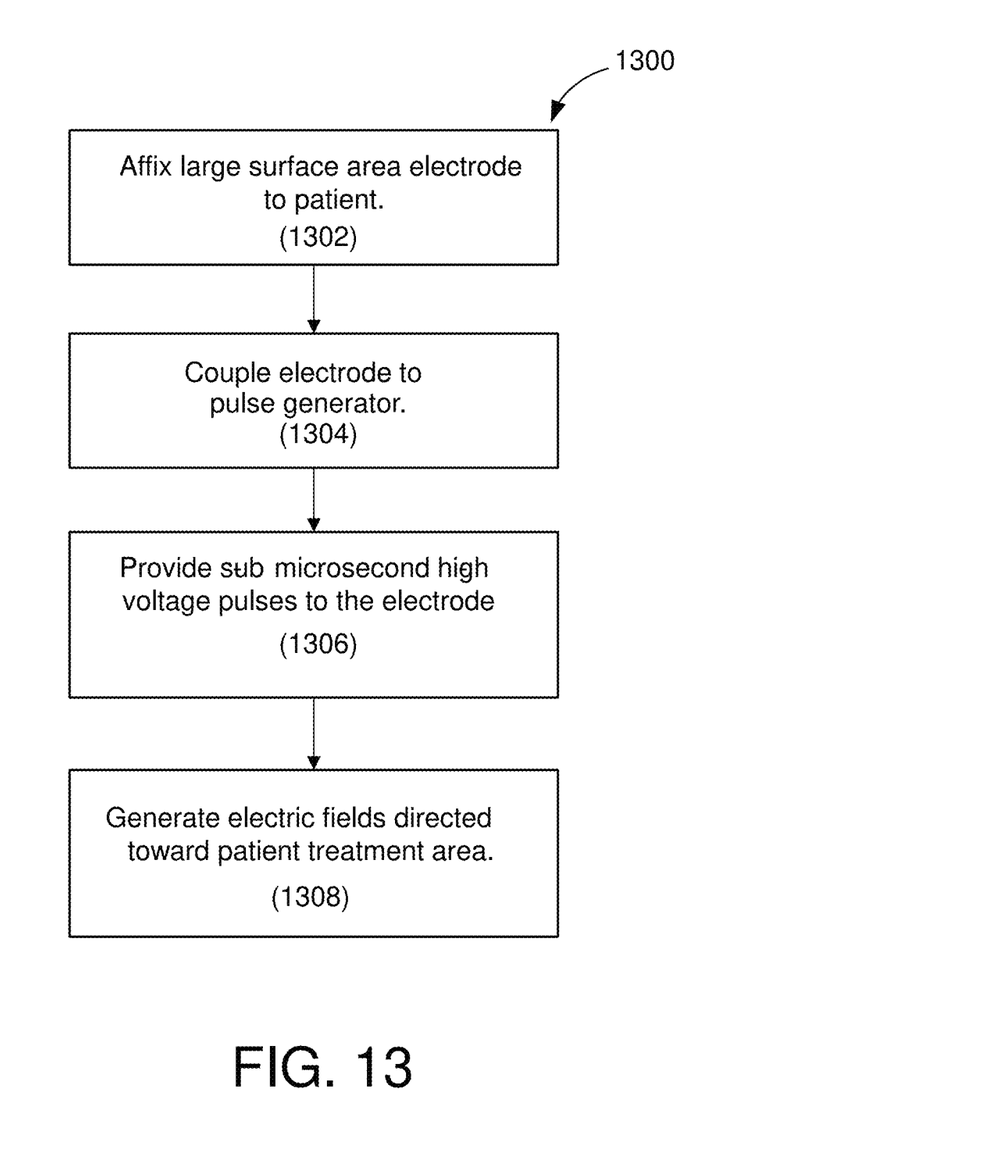
FIG. 13 is a flowchart depicting an example method for delivering sub-microsecond pulsed electrical fields to a patient's treatment area, in accordance with some examples.

FIG. 13 is a flowchart depicting an example of a method 1300 for delivering sub-microsecond pulsed electrical fields to a patient treatment area. Some examples may perform the operations described herein with additional operations, fewer operations, operations in a different order, operations in parallel, and some operations differently. The method 1300 is described below with respect to the system 100 of FIG. 1, however, the method 1300 may be performed by any other suitable system or device.

In FIG. 13, the applicator may be affixed to patient 1302. As described herein, the electrode patterns may be integral with, or coupled to, an applicator 102 that may be applied against the tissue, including but not limited to skin. The applicator may be applied to the tissue by the hydrogel and/or by an adhesive on the surface of the applicator. In some examples, the electrode patterns may be a large surface area electrode pattern similar to the applicators 201, 300, 500, 700, 800, and 900 of FIGS. 2, 3, 5, 7, 8, and 9, respectively. In some other examples, a vacuum may be supplied to the applicator to assist in the attachment of the applicator to the patient's treatment area. In some examples, a vacuum pump may be included within an associated applicator tool (such as the elongate applicator tool 102) or within the housing 105 of the system 100.

The applicator may be coupled to a configurable pulse generator 1304. In some examples the applicator may be pre-coupled to the pulse generator prior to applying to the tissue. In other examples the applicator may be coupled to the pulse generator after applying to the tissue. For example, insulated conductors may be used to couple electrodes of the applicator to the pulse generator 107 of the system.

The pulse generator may then apply sub-microsecond high-voltage energy pulses to the coupled electrodes forming the electrode patterns over the first surface 1306. For example, the pulse generator 107 may provide electrical pulses having a pulse width of between approximately 0.1 ns and 1000 ns. The electrical pulses may be high-voltage pulses having a voltage between approximately several hundred volts and several thousand volts. Advantageously, the arrangement (including the spacing and dimensions) as well as the use of the hydrogel, may prevent or reduce arcing even when applied to the tissue in air with some gaps.

Any of these methods may also include generating sub-microsecond electric fields directed toward the patient treatment area based at least in part on the sub-microsecond high-voltage energy pulses and the applicator. For example, the sub-microsecond high-voltages may generate electric fields through the applicator. In turn, the applicator may direct the electric fields toward the treatment area. In some examples, the generated electric fields may have an electric field density of between 1 kV/cm and 100 kV/cm.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A surface applicator apparatus, the apparatus comprising:
   an insulating substrate extending in a first surface;
   a first electrode forming a first pattern of one or more elongate traces over the first surface, wherein the one or more elongate traces are substantially longer than they are wide;
   a second electrode forming a second pattern of one or more elongate traces over the first surface, wherein the one or more elongate traces are substantially longer than they are wide;
   wherein the one or more elongate traces of the first pattern and the second pattern are adjacent to each other along the lengths of the one or more elongate traces so that there is a uniform gap separating the first pattern from the second pattern along their lengths;
   a first conductor electrically coupled to the first electrode; and
   a second conductor electrically coupled to the second electrode, wherein the first conductor and the second conductor are configured to be placed in electrical communication with a pulse generator configured to deliver sub-microsecond, high-voltage electrical pulses between the first and second electrodes, respectively, and wherein the first and second patterns are configured to form a substantially uniform electrical field over an applicator surface formed by the first and second patterns when sub-microsecond, high-voltage electrical pulses are delivered between the first and the second electrodes.

2. The apparatus of claim 1, further comprising the pulse generator operably connected to the first conductor and the second conductor.

3. The apparatus of claim 1, further comprising one or more vacuum ports on the first surface and a suction channel in communication with the one or more vacuum ports, wherein the one or more vacuum ports are configured to secure the first electrode and the second electrode to a patient treatment area.

4. The apparatus of claim 1, further comprising an insulator within the uniform gap separating the first pattern from the second pattern.

5. The apparatus of claim 4, wherein the insulator comprises an insulating silicone adhesive.

6. The apparatus of claim 1, wherein the first electrode comprises a first electrically conductive hydrogel extending to an outer, tissue-contacting surface, and wherein the second electrode comprises a second electrically conductive hydrogel extending to the outer, tissue-contacting surface.

7. The apparatus of claim 1, wherein the first surface has a surface area of between 25 mm² and 100 cm².

8. The apparatus of claim 1, wherein the one or more elongate traces of the first pattern extend in a length that is greater than 5 times a width of the one or more elongate traces.

9. The apparatus of claim 1, wherein the first electrode comprises a first conductive base region on the first surface in the first pattern and a first conductive hydrogel on the first conductive base region, further wherein the second electrode comprises a second conductive base region on the first surface in the second pattern and a second conductive hydrogel on the second conductive base region.

10. The apparatus of claim 1, wherein the uniform gap separating the first pattern from the second pattern is between 1 mm and 10 mm wide.

11. The apparatus of claim 1, wherein the surface applicator apparatus is flexible.

12. The apparatus of claim 1, wherein the first pattern comprises a first serpentine pattern extending over the first surface and the second pattern comprises a second serpentine pattern extending over the first surface.

13. The apparatus of claim 1, wherein the first pattern and the second pattern are interleaved or interdigitated and separated by the uniform gap.

14. The apparatus of claim 1, wherein the first pattern and the second pattern form a plurality of parallel elongate traces over the first surface.

15. The apparatus of claim 1, wherein a width of the first and the second electrodes and/or the gap between the first and the second electrodes are optimized to provide a consistent field depth to a thickness of a tissue in a treatment area.

16. A system comprising:
an applicator comprising:
an insulating substrate extending in a first surface,
a first electrode forming a first pattern of one or more elongate traces over the first surface, wherein the one or more elongate traces are substantially longer than they are wide,
a second electrode forming a second pattern of one or more elongate traces over the first surface, wherein the one or more elongate traces are substantially longer than they are wide,
wherein the one or more elongate traces of the first pattern and the second pattern are adjacent to each other along the lengths of the one or more elongate traces so that there is a uniform gap separating the first pattern from the second pattern along their lengths,
a first conductor electrically coupled to the first electrode, and
a second conductor electrically coupled to the second electrode; and
a pulse generator configured to generate sub-microsecond high-voltage electric pulses, wherein the first conductor and the second conductor are configured to electrically couple the first electrode and the second electrode to the pulse generator such that a substantially uniform electrical field is formed across the first pattern and the second pattern when sub-microsecond, high-voltage electrical pulses are delivered between the first and the second electrodes.

17. The system of claim 16, wherein the pulse generator further comprises a vacuum pump configured to provide suction to the applicator to secure the applicator to a treatment surface.

18. The system of claim 16, further comprising one or more a vacuum ports on the first surface and a suction channel in communication with the one or more vacuum ports, wherein the one or more vacuum ports are configured to secure the first electrode and the second electrode to a patient treatment area.

19. A method, the method comprising:
affixing a large surface area electrode applicator having a first surface to a patient treatment region; and
applying sub-microsecond pulses between a first electrode forming a first pattern of one or more elongate traces over the first surface and a second electrode forming a second pattern of one or more elongate traces over the first surface, wherein the one or more elongate traces of the first pattern and the one or more traces of the second pattern each have a length that is substantially longer than a width, and are arranged adjacent to each other along their lengths to generate a substantially uniform electric field over the large surface area electrode applicator, wherein the first pattern is adjacent to second pattern so that there is a uniform gap separating the elongate lengths of the first pattern from the elongate lengths of the second pattern.

20. The method of claim 19, wherein affixing comprises adhesively affixing.

21. The method of claim 19, wherein affixing comprises flexing the first surface to conform to the patient treatment region.

22. The method of claim 19, wherein affixing comprises applying suction to secure the first surface to the patient treatment region.

23. The method of claim 19, wherein applying sub-microsecond pulses comprises applying electrical pulses having an amplitude of at least 0.1 kV and a duration of less than 1000 nanoseconds.

24. The method of claim 19, wherein affixing the large surface area electrode to the patient treatment region comprises affixing the large surface area electrode to a skin surface.

25. The method of claim 19, further comprising delivering electric field density based at least in part on the uniform gap.

* * * * *